(12) United States Patent
Damm

(10) Patent No.: US 11,660,181 B2
(45) Date of Patent: May 30, 2023

(54) INTRAOCULAR LENS

(71) Applicant: Carl Zeiss Meditec AG, Jena (DE)

(72) Inventor: Niklas Damm, Berlin (DE)

(73) Assignee: CARL ZEISS MEDITEC AG, Jena (DE)

(*) Notice: Subject to any disclaimer, the term of this patent is extended or adjusted under 35 U.S.C. 154(b) by 0 days.

(21) Appl. No.: 17/907,332

(22) PCT Filed: Mar. 18, 2021

(86) PCT No.: PCT/EP2021/056899
§ 371 (c)(1),
(2) Date: Sep. 26, 2022

(87) PCT Pub. No.: WO2021/191036
PCT Pub. Date: Sep. 30, 2021

(65) Prior Publication Data
US 2023/0112337 A1    Apr. 13, 2023

(30) Foreign Application Priority Data

Mar. 26, 2020   (DE) .................. 10 2020 108 381.5

(51) Int. Cl.
*A61F 2/16*       (2006.01)
(52) U.S. Cl.
CPC ........ *A61F 2/16* (2013.01); *A61F 2002/1683* (2013.01); *A61F 2002/1699* (2015.04); *A61F 2220/0033* (2013.01); *A61F 2250/001* (2013.01)
(58) Field of Classification Search
CPC ...... A61F 2002/1683; A61F 2002/1699; A61F 2/16; A61F 2220/0033; A61F 2250/001
See application file for complete search history.

(56) References Cited

U.S. PATENT DOCUMENTS

| 4,969,897 A | * | 11/1990 | Kalb | ................ A61F 2/161 623/6.45 |
| 5,571,177 A | | 5/1996 | Deacon et al. | |
| 5,567,365 A | | 10/1996 | Weinschenk et al. | |

(Continued)

FOREIGN PATENT DOCUMENTS

EP    0 175 972 A1    4/1986
WO    WO 94/028825 A1    12/1994

OTHER PUBLICATIONS

Office Action of German Application No. 10 2020 108 381.5, dated Feb. 19, 2021.

(Continued)

*Primary Examiner* — William H Matthews
(74) *Attorney, Agent, or Firm* — Alston & Bird LLP

(57) ABSTRACT

The invention relates to an intraocular lens comprising an optics body and a haptic which has a first component with a latching protrusion and a second component with a latching recess, the latching protrusion and the latching recess being arranged at a distance from one another when the haptic is arranged in a relaxed state and being configured to engage with one another when, proceeding from the relaxed state, the haptic is moved in the direction of the optics body into a completely compressed state of the haptic via a partially compressed state of the haptic, the haptic being formed by a single piece and having a haptic cutout which is delimited by the first component and the second component.

7 Claims, 4 Drawing Sheets

(56) References Cited

U.S. PATENT DOCUMENTS

2006/0041308 A1* 2/2006 Nichamin ............. A61F 2/1613
623/6.43
2019/0125523 A1* 5/2019 Barzilay ............... A61F 2/1635

OTHER PUBLICATIONS

PCT International Search Report and Written Opinion of the International Searching Authority, WIPO Application No. PCT/EP2021/056899, dated Jul. 2, 2021.
Written Opinion of the International Searching Authority for PCT/EP2021/056899 (ISA/CN) dated Jul. 2, 2021 (5 pages).

* cited by examiner

INTRAOCULAR LENS

The invention relates to an intraocular lens.

CROSS-REFERENCE TO RELATED APPLICATIONS

The present application is a national phase entry of International Application No. PCT/EP2021/056899, filed Mar. 18, 2021, which claims priority to German Patent Application No. 10 2020 108 381.5, filed Mar. 26, 2020, which are each incorporated herein by reference in their entirety.

An intraocular lens is inserted into the capsular bag of an eye within the scope of a cataract treatment. The intraocular lens has an optics body and a haptic, by means of which the intraocular lens is fastened within the capsular bag. The object of the haptic is to hold the optics body as centrally as possible and with a stable position in the capsular bag. In humans, a capsular bag typically has a diameter ranging from 9.75 mm to 11.0 mm. In a relatively small capsular bag, the haptic tends to be compressed strongly, which may result in an axial offset of the optics body. The axial offset may lead to an uncontrollable and unpredictable change in the optical power of the optics body, which was chosen prior to the cataract treatment, relative to an intraocular lens with a less compressed haptic.

EP 0 175 972 A1 discloses an intraocular lens with a retractable leg.

The problem addressed by the invention is therefore that of developing an intraocular lens which makes it possible to avoid an axial offset of said intraocular lens in a capsular bag of an eye.

The intraocular lens according to the invention comprises an optics body and a haptic which has a first component with a latching protrusion and a second component with a latching recess, the latching protrusion and the latching recess being arranged at a distance from one another when the haptic is arranged in a relaxed state and being configured to engage with one another when, proceeding from the relaxed state, the haptic is moved in the direction of the optics body into a completely compressed state of the haptic via a partially compressed state of the haptic.

By virtue of the latching protrusion and the latching recess engaging in the compressed state, the haptic is more rigid in the compressed state than in the relaxed state or in the partially compressed state. As a result, it is less easy for the haptic to bend in the compressed state, resulting in an axial offset of the optics body being avoidable. Conceivably, the haptic is designed such that it is in the partially compressed state in the case of a relatively large capsular bag, the latter for example having a diameter of more than 10.0 mm, and it is in the compressed state in the case of a relatively small capsular bag, the latter for example having a diameter of less than 10.0 mm.

Preferably, the latching protrusion has a protrusion end face and the latching recess has a recess end face, which is arranged facing the protrusion end face and which is in contact with the protrusion end face in the compressed state. When the haptic is moved in the direction of the optics body proceeding from the relaxed state, the haptic produces an opposite force whose magnitude becomes larger as the haptic is arranged ever close to the optics body. When the recess end face contacts the protrusion end face, this subsequently results in particularly significant increase in the opposite force.

The intraocular lens preferably has a first component end face arranged adjacent to the latching protrusion and a second component end face arranged adjacent to the latching recess, with the first component end face being in contact with the second component end face in the compressed state. When the haptic is moved in the direction of the optics body proceeding from the relaxed state, the haptic produces an opposite force whose magnitude becomes larger as the haptic is arranged ever close to the optics body. When the first component end face contacts the second component end face, this subsequently results in particularly significant increase in the opposite force.

According to the invention, the haptic is formed by a single piece. According to the invention, the haptic has a haptic cutout in this case, the latter being delimited by the first component and the second component. The provision of the haptic cutout causes the region of the haptic arranged adjacent to the haptic cutout to have a weaker embodiment than the remainder of the haptic, resulting in a deformation of the haptic predominantly in this region when the haptic is displaced from the relaxed state into the compressed state via the partially compressed state.

In the relaxed state, the haptic cutout preferably is delimited over its entire edge by the material of the haptic in a plane whose normal is parallel to an optical axis of the optics body. Alternatively, the haptic cutout preferably communicates with the outside of the haptic in a plane whose normal is parallel to the optical axis of the optics body. The haptic cutout is preferably arranged in a haptic region which, proceeding from the optics body, extends to no more than 30% of the overall length of the haptic. The haptic deforming predominantly in the vicinity of the optics body is achieved as a result.

As an alternative to forming the haptic by a single part, the haptic may be formed by two separate parts in an embodiment that is not part of this invention, each of said two separate parts being fastened to the optics body and being arranged at a distance from one another in the relaxed state and in the partially compressed state, with one of the two parts comprising the first component and the other one of the two parts comprising the second component. The one part of the two parts is in contact with the other part of the two parts in the compressed state. The first one of the two parts particularly preferably is the first component. Alternatively, the other one of the two parts particularly preferably is the second component.

The intraocular lens preferably has a first component protrusion, from which the latching protrusion protrudes, and/or a second component protrusion, in which the latching recess is arranged. In particular, choosing the length of the first component protrusion in the direction of the second component protrusion and/or choosing the length of the second component protrusion in the direction of the first component protrusion makes it particularly easily possible to set how far the haptic should be moved in the direction of the optics body in order to attain the compressed state.

Preferably, the latching protrusion has a first protrusion side face and the latching recess has a first recess side face, with, in the compressed state, the first protrusion side face and the first recess side face facing one another and being arranged adjacent to one another. Moreover, the latching protrusion preferably has a second protrusion side face and the latching recess preferably has a second recess side face, with, in the compressed state, the second protrusion side face and the second recess side face facing one another and being arranged adjacent to one another. When the latching protrusion is displaced laterally vis-a-vis the latching recess, the first protrusion side face can abut against the first recess side face or the second protrusion side face can abut against the second recess side face, as a result of which the lateral displacement can be restricted or suppressed.

The intraocular lens preferably has two of the haptics. The two of the haptics can each be fastened to a region of the intraocular lens, with the two regions being arranged facing away from one another.

Preferably, the two of the haptics are arranged symmetrically with respect to one another in relation to the optical axis of the optics body.

The invention is explained in more detail below with reference to the appended schematic drawings.

Figure 1:
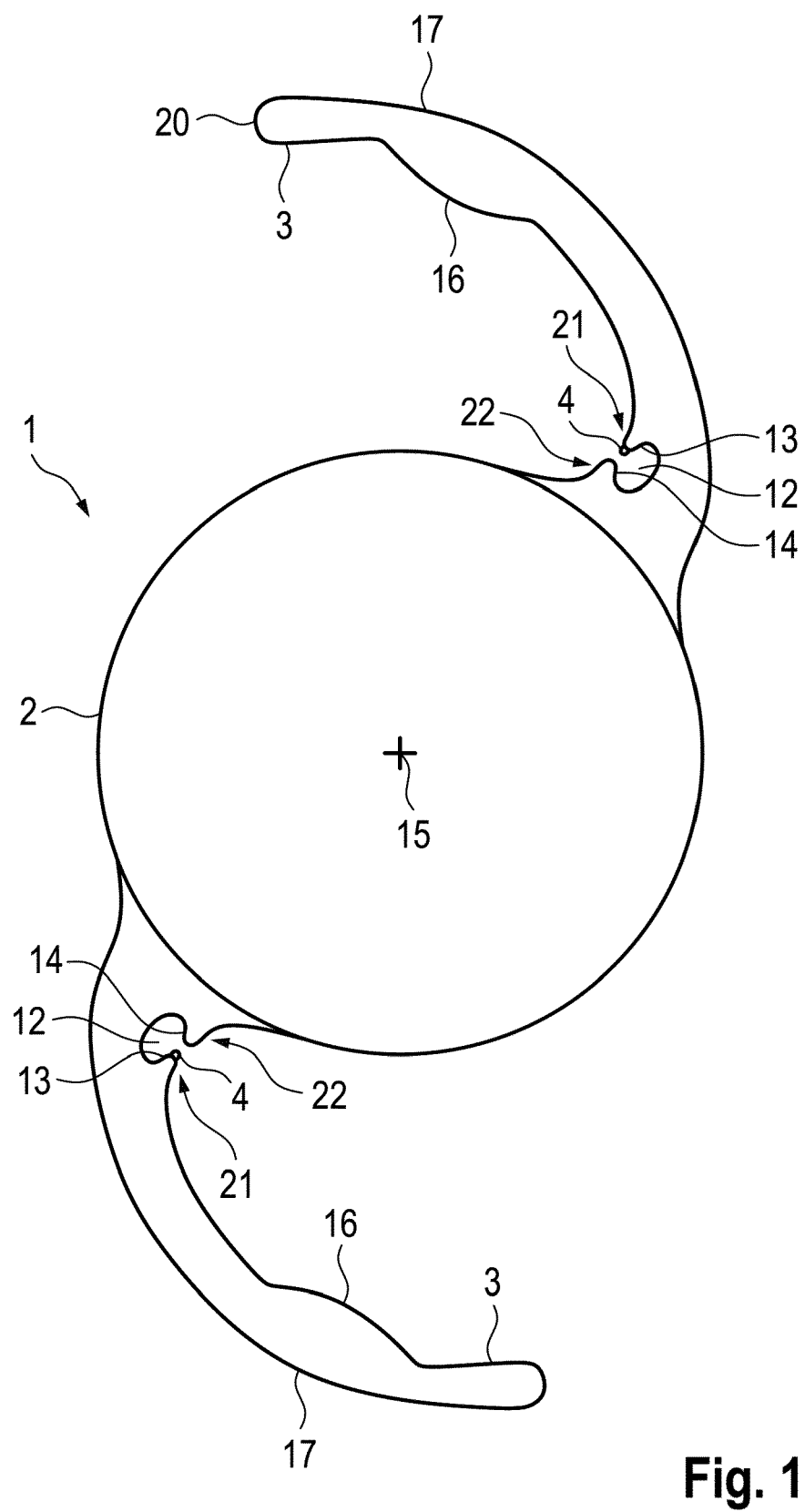
FIG. 1 shows a plan view of a first embodiment of an intraocular lens according to the invention.
Figure 2:
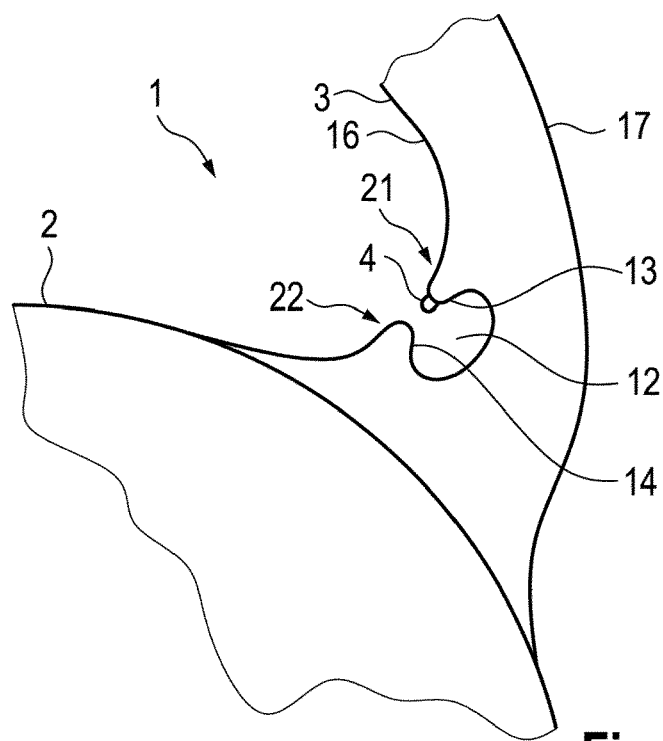
FIG. 2 shows a detail from FIG. 1.
Figure 3:
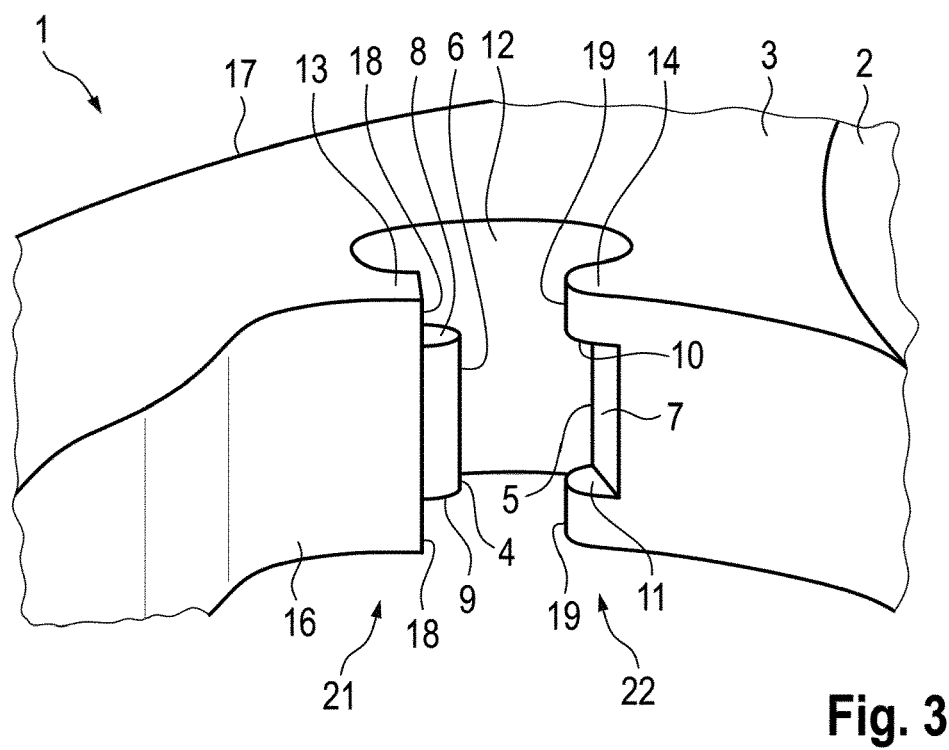
FIG. 3 shows a perspective view of a detail of the first embodiment.

As is evident from FIGS. 1 to 5, an intraocular lens 1 according to the invention comprises an optics body 2 and a haptic 3, which has a first component 21 with a latching protrusion 4 and a second component 22 with a latching recess 5. Alternatively, the first component 21 has the latching recess 5 and the second component 22 has the latching protrusion 4. The latching protrusion 4 and the latching recess 5 are arranged at a distance from one another when the haptic 3 is arranged in a relaxed state of the haptic 3, with FIGS. 1 to 5 showing the haptic 3 in the relaxed state. Moreover, the latching protrusion 4 and the latching recess 5 are configured to be engaged with one another when the haptic 3, proceeding from the relaxed state, is moved in the direction of the optic body 2 into a completely compressed state of the haptic 3 via a partially compressed state of the haptic 3. If the haptic 3 is moved in the direction of the optics body 2 proceeding from the relaxed state, the haptic 3 accordingly initially reaches the partially compressed state, in which the latching protrusion 4 and the latching recess 5 do not yet engage with one another. If the haptic 3 is subsequently moved further in the direction of the optics body 3, the haptic 3 finally reaches the compressed state, in which the latching protrusion 4 and the latching recess 5 engage with one another. FIGS. 1 to 3 show that the first component 21 can be arranged on an inner haptic surface 16, which is arranged facing the optics body 2. Additionally, the haptic 3 has an outer haptic surface 17, which is arranged facing away from the inner haptic surface 16 and which is provided to be in contact with a capsular bag of an eye when the intraocular lens 1 is introduced into the capsular bag.

FIG. 3 shows, by way of example, a latching protrusion 4 and a latching recess 5, as may be installed in all embodiments of the intraocular lens 1. As is evident from FIG. 3, the latching protrusion 4 can taper in the direction of the component, selected from the first component and the second component, which has the latching recess 5. By way of example, the latching protrusion 4 conceivably has the shape of a half cylinder to this end, as is depicted in FIG. 3 for example. However, other shapes are also conceivable, for example a prism or a calotte.

As is evident from FIG. 3, the latching protrusion 4 may have a protrusion end face 6 and the latching recess 5 may have a latching end face 7 which is arranged facing the protrusion end face 6. The recess end face 7 can be in contact with the protrusion end face 6 in the compressed state. Alternatively or in addition, the intraocular lens 1 may have a first component end face 18, which is arranged adjacent to the latching protrusion 4, and a second component end face 19, which is arranged adjacent to the latching recess 5. The first component end face 18 can be in contact with the second component end face 19 in the compressed state.

FIG. 3 shows that the latching protrusion 4 can have a first protrusion side face 8 and the latching recess 5 can have a first recess side face 10, with, in the compressed state, the first protrusion side face 8 and the first recess side face 10 facing one another and being arranged adjacent to one another. Moreover, FIG. 3 shows that the latching protrusion 4 can have a second protrusion side face 9 and the latching recess 5 can have a second recess side face 11, with, in the compressed state, the second protrusion side face 9 and the second recess side face 11 facing one another and being arranged adjacent to one another. The normals of the first protrusion side face 8, of the second protrusion side face 9, of the first recess side face 10 and of the second recess side face 11 can be arranged in parallel with the optical axis 15 of the optics body 2.

FIGS. 1 to 5 show that intraocular lens 1 has a first component protrusion 13, from which the latching protrusion 4 protrudes, and/or a second component protrusion 14, in which the latching recess 5 is arranged.

FIGS. 1 to 3 depict that the haptic 3 is formed by one piece in accordance with the first embodiment of the intraocular lens 1. The haptic 3 has a haptic cutout 12, which is delimited by the first component 21 and the second component 22. In the relaxed state, the haptic cutout 12 communicates with the outside of the haptic 3 in a plane whose normal is parallel to an optical axis 15 of the optics body 2. In this case, the haptic cutout 12 can communicate with the outside of the haptic 3 between the latching protrusion 4 and the latching recess 5. The haptic cutout 12 can be arranged in a haptic region which, proceeding from the optics body 2, extends to no more than 30% of the overall length of the haptic 3. By way of example, the overall length can be defined as the length of a line extending from the optics body 2 to the outer longitudinal end 20 of the haptic 3 in the middle between an inner haptic surface 16, which is arranged facing the optics body 2, and an outer haptic surface 17, which is arranged facing away from the optics body 2.

Figure 4:
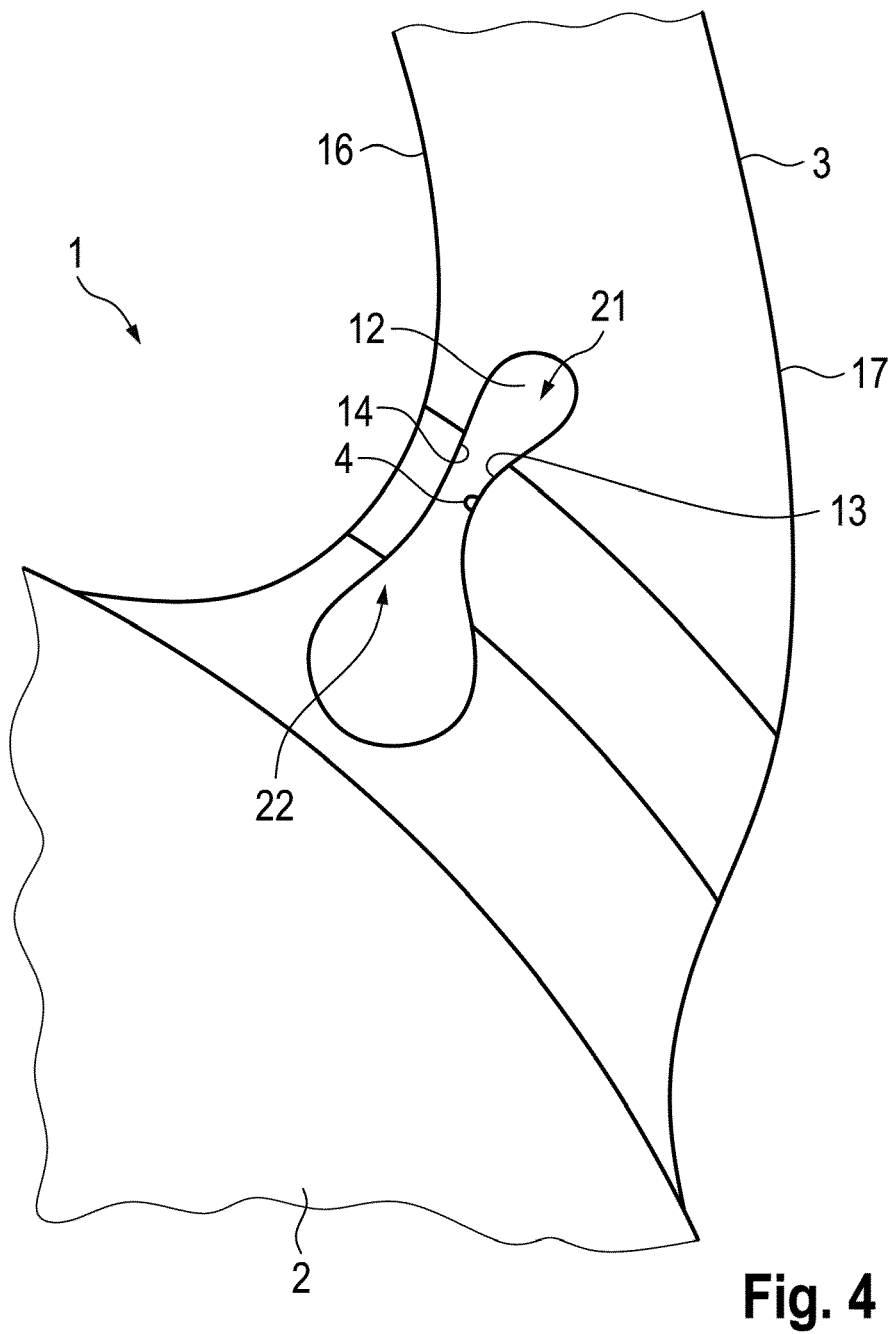
FIG. 4 shows a plan view of a portion of a second embodiment of the intraocular lens according to the invention.

FIG. 4 depicts that the haptic 3 is formed by one piece in accordance with the second embodiment of the intraocular lens 1. In this case, the haptic 3 has a haptic cutout 12, which is delimited by the first component 21 and the second component 22. In the relaxed state, the haptic cutout 12 is delimited over its entire edge by the material of the haptic 3 in a plane whose normal is parallel to an optical axis 15 of the optics body 2. The haptic cutout 12 can be arranged in a haptic region which, proceeding from the optics body 2, extends to no more than 30% of the overall length of the haptic 3. By way of example, the overall length can be defined as the length of a line extending from the optics body 2 to the outer longitudinal end 20 of the haptic 3 in the middle between an inner haptic surface 16, which is arranged facing the optics body 2, and an outer haptic surface 17, which is arranged facing away from the optics body 2.

Figure 5:
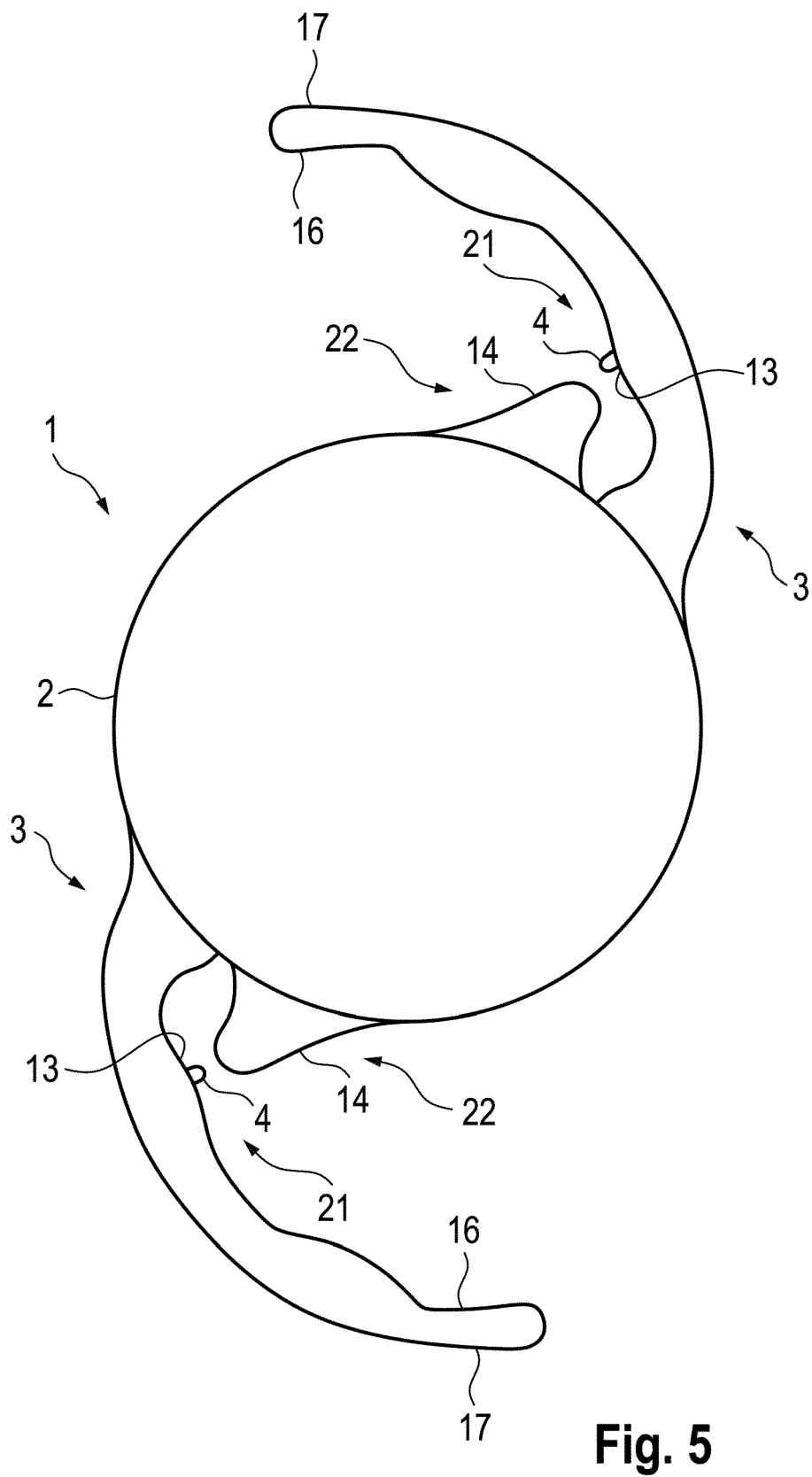
FIG. 5 shows a plan view of a third embodiment of the intraocular lens, the third embodiment not being part of this invention.

FIG. 5 illustrates that, according to the third embodiment of the intraocular lens 1 not part of the invention, the haptic 3 may be formed by two separate parts, each of said two separate parts being fastened to the optics body 2 and being arranged at a distance from one another in the relaxed state and in the partially compressed state, with one of the two parts comprising the first component 21 and the other one of the two parts comprising the second component 22. Here, the other of the two parts conceivably is the second component 22, as is also depicted in FIG. 5. Alternatively, the first one of the two parts conceivably is the first component 21.

FIGS. 1 and 5 depict that the intraocular lens 1 may have two of the haptics 3. The two of the haptics 3 can be fastened to a respective region of the intraocular lens 1, with the two regions being arranged facing away from one another. Moreover, FIGS. 1 and 5 show that the two of the haptics 3 can be arranged symmetrically with respect to one another in relation to the optical axis 15 of the optics body 2.

LIST OF REFERENCE SIGNS

1 Intraocular lens
2 Optics body
3 Haptic
4 Latching protrusion
5 Latching recess
6 Protrusion end face
7 Recess end face
8 First protrusion side face
9 Second protrusion side face
10 First recess side face
11 Second recess side face
12 Haptic cutout
13 First component protrusion
14 Second component protrusion
15 Optical axis
16 Inner haptic surface
17 Outer haptic surface
18 First component end face
19 Second component end face
20 Longitudinal end
21 First component
22 Second component

The invention claimed is:

1. Intraocular lens comprising an optics body and a haptic which has a first component with a latching protrusion and a second component with a latching recess, the latching protrusion and the latching recess being arranged at a distance from one another when the haptic is arranged in a relaxed state and being configured to engage with one another when, proceeding from the relaxed state, the haptic is moved in the direction of the optics body into a completely compressed state of the haptic via a partially compressed state of the haptic, the haptic being formed by a single piece and having a haptic cutout which is delimited by the first component and the second component.

2. Intraocular lens according to claim 1, wherein the latching protrusion has a protrusion end face and the latching recess has a recess end face, which is arranged facing the protrusion end face and which is in contact with the protrusion end face in the compressed state.

3. Intraocular lens according to claim 1, wherein the intraocular lens has a first component end face arranged adjacent to the latching protrusion and a second component end face arranged adjacent to the latching recess, with the first component end face being in contact with second component end face in the compressed state.

4. Intraocular lens according to claim 1, wherein, in the relaxed state, the haptic cutout is delimited over its entire edge by the material of the haptic in a plane whose normal is parallel to an optical axis of the optics body or said haptic cutout communicates with the outside of the haptic in the plane whose normal is parallel to the optical axis.

5. Intraocular lens according to claim 1, wherein the haptic cutout is arranged in a haptic region which, proceeding from the optics body, extends to no more than 30% of the overall length of the haptic.

6. Intraocular lens according to claim 1, wherein the intraocular lens has a first component protrusion, from which the latching protrusion protrudes, and/or a second component protrusion, in which the latching recess is arranged.

7. Intraocular lens according to claim 1, wherein the latching protrusion has a first protrusion side face and the latching recess has a first recess side face, with, in the compressed state, the first protrusion side face and the first recess side face facing one another and being arranged adjacent to one another.

* * * * *